(12) United States Patent
Ross

(10) Patent No.: US 7,376,457 B2
(45) Date of Patent: May 20, 2008

(54) UTILIZATION OF HEART RATE VARIABILITY IN ANIMALS

(76) Inventor: Christine Ross, P.O. Box 508, Del Mar, CA (US) 92014

( * ) Notice: Subject to any disclaimer, the term of this patent is extended or adjusted under 35 U.S.C. 154(b) by 150 days.

(21) Appl. No.: 10/378,341

(22) Filed: Mar. 3, 2003

(65) Prior Publication Data

US 2004/0019289 A1    Jan. 29, 2004

Related U.S. Application Data

(60) Provisional application No. 60/360,930, filed on Mar. 1, 2002.

(51) Int. Cl.
*A61B 5/04* (2006.01)

(52) U.S. Cl. .................................... 600/515
(58) Field of Classification Search ............ 600/519, 600/515, 509, 301; 128/898
See application file for complete search history.

(56) References Cited

U.S. PATENT DOCUMENTS

| | | | |
|---|---|---|---|
| 5,105,354 A | | 4/1992 | Nishimura |
| 5,201,321 A | * | 4/1993 | Fulton ..................... 600/515 |
| 5,365,426 A | | 11/1994 | Siegel et al. |
| 5,560,370 A | * | 10/1996 | Verrier et al. ............. 600/518 |
| 6,144,878 A | * | 11/2000 | Schroeppel et al. ........ 600/515 |
| 6,212,427 B1 | | 4/2001 | Hoover |
| 6,301,499 B1 | | 10/2001 | Carlson et al. |
| 6,330,469 B1 | | 12/2001 | Griffen et al. |
| 7,252,637 B2 | * | 8/2007 | Ebner et al. ............... 600/301 |

OTHER PUBLICATIONS

E. Mohr et al., "Heart rate variability A noninvasive approach to measure stress in calves and calves", Physiology & Behavior 75 (2002) 251-259, Elsevier.
International Search Report for PCT Application No. PCT/US03/06431.
Tygesen et al., "Intensive home-based exercise training in cardiac rehabilitation increases exercise capacity and heart rate variability", Int. J. Cardiol. Jul. 2001, 79(2-3): 175-82, abstract only.
Matsunaga et al., "Spectral analysis of circadian rhythms in heart rate variability of dogs", abstract only, Am J Vet Res. Jan. 2001; 62(1):37-42.

(Continued)

*Primary Examiner*—George Manuel
(74) *Attorney, Agent, or Firm*—Townsend and Townsend and Crew LLP

(57) ABSTRACT

Provided is a method for detection of a preselected condition such as subclinical stress or pain in a subject animal using heart rate variability. The method comprises the steps of determining a heart rate and/or inter-beat interval for the subject animal over a preselected period of time to determine the subject animal's heart rate data. The method further comprises analyzing the heart rate or inter-beat data from the subject animal to identify a set of heart rate variability data for the subject animal for a selected heart rate variability parameter such as a frequency domain or time domain parameter such as LF/HF ratio. The heart rate variability data from the selected animal can be compared to substantially normal values established for the selected animal species or compared to the subject animal's own previously identified substantially normal values or HRV pattern over a period of time and thereby determine whether the preselected condition exists.

34 Claims, 2 Drawing Sheets

OTHER PUBLICATIONS

Kawase et al., "Heart rate variability during massive hemorrhage and progressive hemorrhagic shock in dogs", Can J Anaesth Aug. 2000: 47(8):807-14.

"Heart rate variability in BSE", Vet Rec. Dec. 21-28, 1996, 139(25):631, reference only.

Jonker et al., "Chataracteristics of fetal heart rate changes during the expulsive stage of bovine parturition in relation to fetal outcome", abstract only, Am J. Vet Res., Sep. 1996, 57(9):1373-81.

Physick-Sheard et al., "Frequency domain analysis of heart rate variability in horses at rest and during exercise", Equine Vet J. May 2000, 32(3):253-62.

Kuwahara et al., "Influence of training on autonomic nervous function in horses: evaluation by power spectral analysis of heart rate variability", Equine Vet J Suppl. Jul. 1999, 30:178-80.

Thayer et al., "Heart rate variability in the horse by ambulatory monitoring", Biomed Sci Instrum. 1997, 33:482-5.

Thayer et al., "Heart rate variability during exercise in the horse", Biomed Sci Instrum 1997, 34:246-51, abstract only.

M. Bowen, "Heart Rate Variability", Cardiology of the Horse, Ch. 11: 161-76, 1999.

"Heart rate variability in Doberman Pinchers with and without echocardiographic evidence of dilated cardiomyopathy", Am J Vet Res. May 2000, 61(5):506-11, abstract only.

C.A. Calvert, "Heart rate variability", Vet Clin North Am Small Animal Pract. Nov. 1998: 28(6):1409-27, viii, abstract only.

Minors et al., "Heart rate variability in the dog: is it too variable?", Can J. Vet Res., Apr. 1997, 61(2):134-44, abstract only.

Houle et al., "Low-frequency component of the heart rate variability spectrum: a poor marker of sympathetic activity", abstract only, Am J. Phisiol. Jan. 1999:276(1Pt2:H215-23.

V. Pougatchev et al., "Biocom Heart Rhythm Scannerusers Manual,"Heart Rate Variability Analysis Systems Users Manual, Version 2.0, www.biocomtech.com, 1998-2002.

Ohmura et al., "Effects of Atropine Injection on Heart Rate Variability in Thoroughbred Horses", J. Vet. Med. Sci. 63(12): 1359-1360 (2001).

* cited by examiner

UTILIZATION OF HEART RATE VARIABILITY IN ANIMALS

The present application claims the benefit of priority of U.S. provisional patent application No. 60/360,930, filed Mar. 1, 2002.

FIELD OF THE INVENTION

The present invention relates generally to the field of utilizing heart rate variability analysis in animals. In particular, the present invention relates to novel devices and methods for analysis and utilization of heart rate variability in animals. More particularly, the present invention relates to methods for analyzing the health and/or well being of companion, competition, confinement and/or food producing animals and for diagnosis, treatment and/or prevention of disease in such animals.

BACKGROUND OF THE INVENTION

Will Rogers once stated: "Personally I have always felt that the best doctor in the world is the Veterinarian, for he can't ask his patients 'What is the matter . . . ?', he's just got to know." Since the inception of veterinary medicine, the veterinarian has been forced to rely on a keen sense of observation and assessment of clinical parameters for evaluation of his/her patients in the diagnosis and treatment of disease. Over the years and often on the heels of human medicine, many clinical tools, diagnostic and/or prognostic parameters and modalities have developed for assessment of these clinical parameters and hence evaluation of the health status of an animal.

Heart rate variability (HRV) generally refers to the beat-to beat fluctuations in heart rate (e.g., variation in R-R interval) that occur as a normal physiological response, e.g., an internal response to neuronal or endocrine influence, or variations in heart rate that occur in response to external stimuli. In general, heart rate variability reflects non-invasively the autonomic nervous system activity, e.g., the sympathetic and parasympathetic influences upon heart beat rate and rhythm.

In human medicine, the most studied body systems in HRV analysis are: the respiratory system and its effect on HRV known as respiratory sinus arrhythmia; the vasomotor system and baroreceptor variation in heart rate and blood pressure, e.g., Mayer waves; the thermoregulatory system; the renin-angiotensin system and the central nervous system. At present, in human medicine, it can generally be stated that greater variability in heart rate indicates a better state of health for the autonomic nervous and/or cardiac systems (see, e.g., petrus.upc.es/wwwdib/bio/heart_rat_var/pruebas/hrv1.html).

In human medicine, heart rate variability has been studied or used in the prognosis of sudden cardiac death and for the diagnosis of subacute and potentially catastrophic illness. In U.S. Pat. No. 6,330,469 to Griffen et al., HRV has been used in a method to access the health status of premature newborn infants and for the early detection of catastrophic illness in a patient. Likewise, U.S. Pat. No. 5,105,354 to Nishimura discloses a method for evaluation of respiration and heart beat which permits one to forecast sudden infant death syndrome (SIDS).

Heart rate variability has also been used in human medicine as an indicator of exercise capacity. U.S. Pat. No. 6,301,499 to Carlson et al., discloses a method for correlation of $VO_{2.max}$ with HRV for determining exercise capacity in patients with congestive heart failure (CHF). Tygesen et al. in "Intensive home-based exercise training in cardiac rehabilitation increases exercise capacity and heart rate variability" (*Int J Cardiol.* 2001 July; 79(2-3):175-82) disclose that intensive exercise training in cardiac rehabilitation increases exercise capacity and global HRV, which could be of prognostic significance.

Various systems for determination of and/or monitoring HRV in human patients have been described, see, e.g., U.S. Pat. No. 6,212,427 to Hoover which discloses a rather cumbersome apparatus designed to be worn by the patient comprised of an output device requiring a plurality of properly placed electrodes for generation of an electrical signal from the patient's heart.

In veterinary medicine, prior to the present invention, the limited attempts at utilization of heart rate variability have produced variable results. For example, in "Spectral analysis of circadian rhythms in heart rate variability of dogs" (*Am J Vet Res.* 2001 January; 62(1):37-42), Matsunaga et al. disclose that power spectral analysis of HRV may be useful as a noninvasive technique for assessing the effect of drugs on activity of the autonomic nervous system in dogs. Likewise, Kawase et al. in "Heart rate variability during massive hemorrhage and progressive hemorrhagic shock in dogs" (*Can J Anaesth* 2000 August: 47(8):807-14) disclose that HRV could be a valuable tool in assessing various degrees of hemorrhagic shock.

In food producing animals, heart rate variability has been studied in cattle with BSE (see, e.g., "Heart rate variability in BSE", *Vet Rec.* 1996 December 21-28; 139(25):631) and during parturition in cattle (see, Jonker et al., "Characteristics of fetal heart rate changes during the expulsive stage of bovine parturition in relation to fetal outcome", *Am J Vet Res.* 1996 September; 57(9): 1373-81).

Likewise, limited analysis of heart rate variability has been conducted in the horse. For example, Physick-Sheard et al. indicate that frequency and power spectral analysis of HRV may be a method for assessing exercise response to experimental manipulations and disease states in the horse (Physick-Sheard et al., "Frequency domain analysis of heart rate variability in horses at rest and during exercise", *Equine Vet J.* 2000 May;32(3):253-62).

Kuwahara et al., and Thayer et al. report that the equine heart may be largely controlled by parasympathetic activity and disclose a decrease in HRV by training, rather than an expected increase as seen in human counterparts (See, Kuwahara et al., "Influence of training on autonomic nervous function in horses: evaluation by power spectral analysis of heart rate variability.", *Equine Vet J Suppl.* 1999 July; 30:178-80; Thayer et al., "Heart rate variability in the horse by ambulatory monitoring", *Biomed Sci Instrum.* 1997; 33:482-5; and also Thayer et al., "Heart rate variability during exercise in the horse.", *Biomed Sci Instrum.* 1997; 34:246-51). Prior to the present invention, perhaps one of the more definitive works for heart rate variability in the horse set forth by Mark Bowen (Bowen, M., "Heart Rate Variability", *Cardiology of the Horse*, Ch. 11: 161-76, 1999 W. B. Saunders (ed. by Celia Marr)), acknowledged the largely experimental nature of the use of this modality in the horse and notes that little work has been actually been done in the horse.

Moreover, much of the work done in animals cites confusing, if not disappointing results. For example, in "Heart rate variability in Doberman Pinschers with and without echocardiographic evidence of dilated cardiomyopathy" (*Am J Vet Res.* 2000 May; 61(5):506-11) Calvert & Jacobs disclose that HRV as a diagnostic tool in animals has important limitations and that better noninvasive tests of autonomic function are needed. Likewise, Calvert demonstrated that HRV analysis in the dog is confounded by pronounced sinus arrhythmia and may not have clinical utility as a diagnostic technique in dogs (see, "Heart rate variability", Calvert, C. A., *Vet Clin North Am Small Animal Pract.* 1998 November: 28(6):1409-27, viii). See also, Minors & O'Grady, "Heart rate variability in the dog: is it too variable?", *Can J Vet Res.* 1997 April; 61(2):134-44.

Animal studies with dogs at Ohio State University indicated that the low frequency component of the HRV spectrum (0.06-0.10 Hz), often used as an "accurate" reflection of sympathetic activity, does not correlate with interventions which enhance cardiac sympathetic drive, e.g., exercise and myocardial ischemia (which should elicit increases in the low-frequency power). In these studies, the low frequency power decreased rather than increased and, as such, does not accurately reflect changes in sympathetic activity (see, Houle & Billman, "Low-frequency component of the heart rate variability spectrum: a poor marker of sympathetic activity", *Am J Physiol.* 1999 January: 276(1Pt2:H215-23). Thus, there still exists a need in the art for a device and method which enables convenient, accurate, and meaningful analysis of such HRV parameters in animals.

In addition, prior to the present invention there has been little to no work done with respect to HRV as a clinical tool for assessment and management of stress in animals, especially animals reared in confinement or for companion animals, e.g., in pets exposed to separation anxiety. Likewise, prior to the present invention, the art has been virtually devoid of information relative to providing effective noninvasive management of pain in animals utilizing HRV. Accordingly, there exists a need in the art for a device and method which enables a veterinarian, or other user, to accurately, conveniently and efficiently assess pain and well being in animals and for diagnosis of disease conditions and for clinical evaluation of efficacy of therapeutic measures to eliminate or manage the same.

OBJECTS OF THE INVENTION

It is an object of the invention to provide a device and method which enables a veterinarian to accurately, conveniently and efficiently assess pain and well being in animals and for diagnosis of disease conditions and for clinical evaluation of efficacy of therapeutic measures to eliminate or manage such conditions.

It is a further object of the invention to provide a device and method for assessment and management of stress in animals, especially animals reared in confinement housing, e.g., a feeder swine or poultry laying house operation.

Another object of the invention is to provide a device and a method for enclosure evaluation for animals reared in or otherwise contained in confinement housing e.g., for determination of optimal breeding conditions (especially for exotic and endangered animal species).

It is a also an object of the invention to provide a device and method for assessment and management of stress in animals, especially for companion animals, e.g., stress levels in pets exposed to separation anxiety.

Yet another object of the invention is to provide a device and method which enables real time assessment of aerobic fitness and/or exercise conditioning in athletic animals, e.g., in racing animals such as dogs and horses.

A further object of the invention is to provide a device and method enabling biofeedback of HRV as a tool to train animals through Pavlovian conditioning to positively influence the autonomic nervous system, e.g., to train an animal to calm itself thereby reducing stress, and/or to manage unacceptable behavioral vices such as cribbing, weaving, barking and the like.

An additional object of the invention is to provide a device and method for localization of pathologic lesions or a source of pain, e.g., for diagnosis and localization of a lameness producing lesion.

SUMMARY OF THE INVENTION

In one embodiment, the present invention provides a method for detection of a preselected condition such as e.g., subclinical stress or subclinical pain in a subject animal using heart rate variability analysis. In one embodiment, the method comprises the steps of determining a heart rate and/or inter-beat interval for the subject animal over a preselected period of time to determine the subject animal's heart rate data. The heart rate data can be detected and analyzed from an ECG or PPG signal received from a signal detection means located on the animal. The method further comprises analyzing the collected heart rate or inter-beat data from the subject animal via spectral analysis to identify a set of heart rate variability data for the subject animal for a selected heart rate variability parameter such as a frequency domain or time domain parameter such as LF/HF ratio. The heart rate variability data from the selected animal can be compared to substantially normal values established for the selected animal species or compared to the subject animal's own previously identified substantially normal values or HRV pattern over a period of time and thereby determine whether the preselected condition exists.

In another embodiment, the invention provides a device and method enabling biofeedback of HRV as a tool to train animals through Pavlovian conditioning to positively influence the autonomic nervous system, e.g., to train an animal to calm itself thereby reducing stress, and/or to manage unacceptable behavioral vices such as cribbing, weaving, barking and the like.

DETAILED DESCRIPTION OF THE INVENTION

Figure 1:
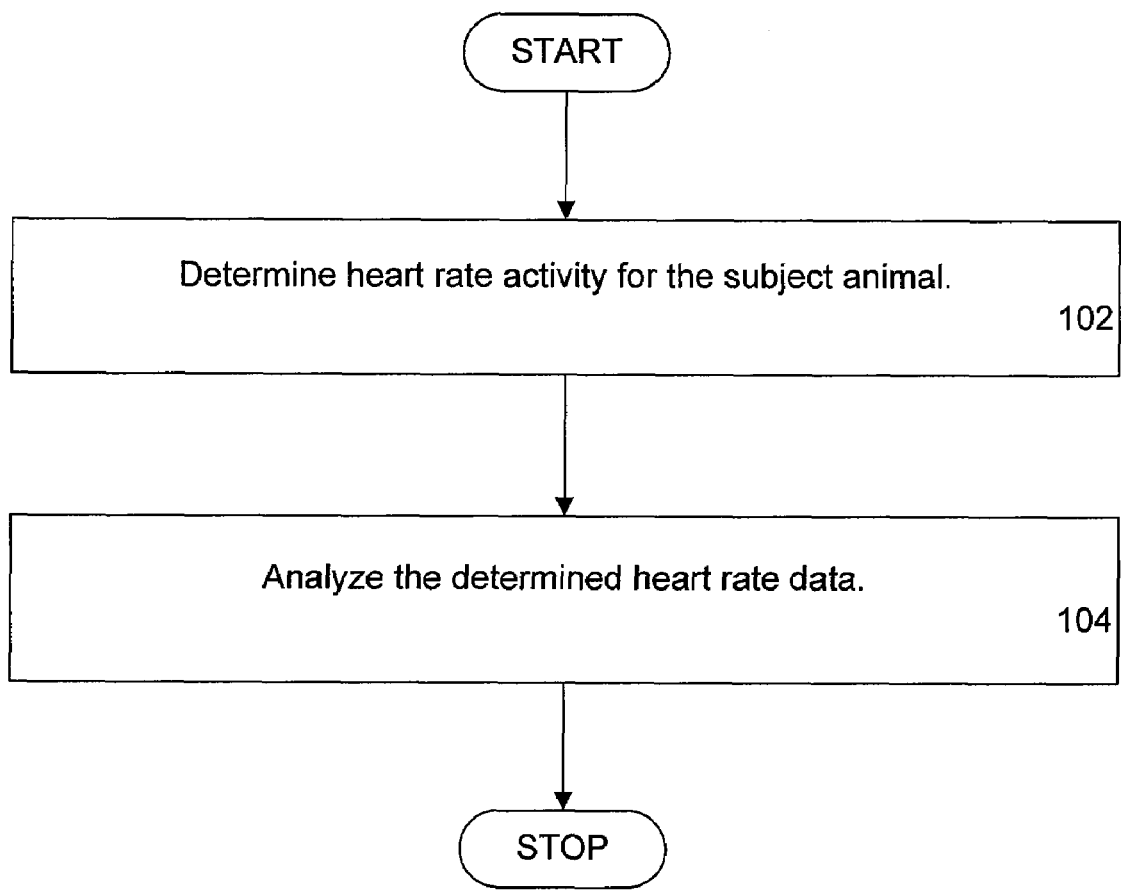
FIG. 1 is a flow diagram of operations performed in accordance with the present invention.

Additional objects, advantages and other novel features of the invention will be set forth in part in the description that follows and in part will become apparent to those skilled in the art upon examination of the foregoing or may be learned with the practice of the invention. Additionally, throughout this document, various publications and patents have been cited, the contents of which are incorporated herein by reference in their entirety.

Set forth in greater detail below are specific details related to novel devices and methods for utilizing heart rate variability analysis in animals. In particular, the present invention provides specific teachings related to novel devices and methods for collection of and analysis and utilization of heart rate variability data in animals to diagnose and/or prevent disease or to monitor and/or improve the state of well being in the subject animal. The examples set forth herein are in no way intended to limit the scope of the invention. Those of skill in the art will realize that, given the teachings provided herein, many variations of the methods are possible that will fall within the scope of the invention.

Briefly, in one embodiment, the device of the invention comprises a means for detection of electrical activity of the heart such that heart rate and/or inter-beat intervals can be accurately determined. The heart rate detection means can range from a standard externally applied electrocardiographic recording device designed for use in detecting and reproducing an electrocardiogram (ECG) signal generated from the heart, e.g., a Holter system similar to the type set forth in Bowen, M., "Heart Rate Variability", *Cardiology of the Horse*, Ch. 11: 161-76, (1999) W. B. Saunders. Although many devices currently exist which can provide means for detection of the electrical activity of the heart, one important feature of the detection means of the instant invention is in the accurate detection of the QRS complexes and, in particular, the R wave component of the signal such that an accurate R-R interval can be ascertained by algorithmic or other analysis of the detected signal.

Alternatively, heart rate and inter-beat time intervals can be detected via utilization of a signal detection means which measures peripheral blood flow to the extremities such as a photoplethysmograph (PPG) or pulse wave sensor. Briefly, the PPG utilizes a photocell which converts light into electrical energy. A beam of infrared light is projected through a selected body tissue and toward the photocell. The amount of light reaching the photocell is inversely proportional to the amount of blood within the tissue and can be used to record these changes which reflect heart rate and inter-beat intervals similar to the inter-beat intervals of the ECG. One of skill in the art can appreciate that the heart rate or signal detection means can be removably attached to the subject animal or can be implanted at a desired location within the animals body, e.g., subcutaneously or internalized via swallowing or oral ingestion of the signal detection means as set forth in certain of the telemetric monitoring systems referenced herein.

Associated with the heart rate detection means is a means for recording or storing the detected ECG or PPG signal. The recording means can be selected from among any of a number of commercially available units. Alternatively, the detection means and recording or data storage means and can be incorporated into the a single device which detects and records the ECG or PPG signal. ECG or PPG signal recordings can be analog or digital and can be recorded as with e.g., the Holter system or pulse wave sensor, or transmitted from the detection means via, e.g., radiotelemetry directly into a remote recording device where the signal is stored and/or analyzed via commercially available software, e.g., from Biocom Technologies, Seattle, Wash. (see, e.g., www.biocomtech.com).

As set forth more fully herein and as can be appreciated by one of skill in the art, algorithmic software for spectral analysis of the detected ECG or PPG signal can be modified or adjusted or otherwise adapted to suit the species or subject animal of interest. For example, the human HRV variability analysis software available from Biocom Technologies can be modified or adapted for use in analysis of HRV data in a selected species of animal, e.g. for use on a horse or dog (see, Pougatchev, Vadim et al.; BIOCOM HEART RHYTHM SCANNER USERS MANUAL, "Heart Rate Variability Analysis System Users Manuel, Version 2.0"; www.biocomtech.com (1998-2002) the contents of which are hereby incorporated herein by reference. Briefly, data (ECG or PPG signals) can be collected for a preselected period of time from a pool of substantially normal and unstressed animals. The collected data can be analyzed via spectral analysis to establish substantially normal values and ranges for any of a number of selected variables of time domain or frequency domain such as high frequency (HF) or low frequency (LF) signals of the recorded signal as set forth more fully below. For example, ranges for normal LF and HF of the recorded ECG signals can be established for the species of interest. (See, e.g., Ohmura et al, "Effects of Atropine Injection on Heart Rate Variability in Thoroughbred Horses" *J. Vet. Med. Sci.* 63(12): 1359-1360 (2001) which cites one set of normal HF and LF power ranges. These normal ranges can then be used for comparison and/or analysis HRV data collected from a subject animal of the selected species for use in the methods set forth herein, e.g., for use in a method of evaluation of stress or fitness evaluation and the like.

A variety of commercially available telemetry systems are available which utilize external as well as internal signal detection means (transmitters) and, depending upon the selected animal, can be modified, or otherwise adapted for use in the methods set forth herein. Examples of telemetry monitoring systems include the externally applied monitor and telemetry acquisition systems from Polar® Heart Rate Monitors (www.horsebeat.co.uk), the implantable data and telemetry acquisition systems from Data Sciences International (DSI™; www.datasci.com) and Lotek Wireless Inc. (www.lotek.com) or NASA telemetry monitoring systems (www.nasa.gov) and the like. In a preferred embodiment, the invention provides a noninvasive telemetric device for small animals that (e.g., companion animals such as dogs and cats) is conducive to home use (e.g., a collar-type device) for, e.g., out patient monitoring.

The collected ECG or PPG signal can be analyzed for a preselected period of time utilizing a variety of parameters including but not limited to: time domain parameters such as heart rate (mean heart rate averaged over a selected time, beats per minute (BPM)); mean NN which is a mean inter-beat interval value averaged over the preselected period of time; and the SDNN which is a standard deviation of the NN intervals derived from calculating the square root of their variance. The collected ECG or PPG signal can likewise be analyzed for a preselected period of time utilizing a variety of frequency domain parameters including, but not limited to: the total power (TP), very low frequency signals (VLF); low frequency signals (LF); high frequency signals (HF); LF/HF ratio which measures the overall balance of the autonomic nervous system between the sympathetic and parasympathetic components; and normalized values for high and low frequency. The HF and LF components of the spectral analysis can be used in a comparison over the duration of the preselected recording time (e.g. a 5-10 minute recording or a 24 hour Holter-type recording) to determine the overall balance of the autonomic nervous system, e.g., the relative amount of HF signal to LF signal. This balance profile can also be compared with the SDNN to determine the relative total power or robustness of the autonomic nervous system for the selected animal.

The present invention provides a method of assessing HRV in a selected animal utilizing one or more of the above-described parameters which will enable a veterinarian to accurately, conveniently and efficiently assess, e.g., pain and/or the well being in animals, for diagnosis of disease conditions and for clinical evaluation of efficacy of therapeutic measures to eliminate or manage a particular condition. One of skill in the art can appreciate that, given the teachings set forth herein, the devices and methods can be readily adapted to include any of a number of selected animal species including, but not limited to, horses, dogs, cats, cows, pigs, chickens, sheep, goats and other domestic livestock or companion animals. The devices and methods set forth herein are also meant to be adaptable for and to include exotic animal species and aquatic or marine animals as well as laboratory animals and other animals reared or housed in confinement. In addition, telemetrically monitoring sentinel animals in wild animal preserves and monitoring environmental changes and impact on ecosystems via sentinel animals in the wild are also contemplated.

In one embodiment of the invention, a method for detection of pain in a preselected animal is provided which is comprised of establishing a normal R-R interval and/or other HRV data and/or indices from the preselected animal (or a predicted normal HRV for the animal species); monitoring the HRV of preselected animal for changes in HRV which are indicative of pain. In general, an animal under the influence of a painful stimulus will elicit changes in HRV, e.g., a change in R-R interval and/or other HRV indices such as an increase in LF power output which is indicative of the effect of a painful stimulus and sympathetic output in response to the pain.

While not wishing to be bound by any particular theory, in humans, e.g., when the parasympathetic system is dominant, the heart inter-beat levels (IBI) are oscillating with higher frequency (e.g., 0.15-0.4. Hz). When sympathetic arousal occurs, the lower frequency oscillations take place. The low frequency range (e.g., 0.4-0.15 Hz) of the IBI power spectrum displays sympathetic influence. The low frequency/high frequency ratio is used to show the balance between both branches of the autonomic nervous system. Given the teachings set forth herein, the response and optimal balance which is species specific can be determined for the selected animal species and a subject animal then monitored accordingly.

The method further can comprise identification of the etiologic agent which is responsible for the pain in the selected animal and attenuating and/or removal of the etiologic agent or treatment with a suitable drug or other therapeutic modality to reduce the level of pain seen in the animal via continued monitoring of HRV status. Real time HRV can be monitored before, during and after specific therapies to determine therapeutic efficacy. Subsequent HRV readings would indicate the long term efficacy and lasting effects of therapeutic or ameliorative treatment measures.

For example, a selected animal's HRV could be monitored (e.g., postsurgically) to determine pain levels and thereby dictate administration of pain medication and case management. In addition, e.g., as an adjunct in lameness diagnosis and treatment, in conjunction with clinical examination, flexion tests, palpation, manipulation, and movement, real time HRV fluctuations can be used to indicate pain and/or stress response in the selected animal (patient) in response to specific clinical diagnostic measures. Assessment of HRV fluctuations can also be used as an adjunct in the diagnosis of neuropathy. HRV can be monitored in conjunction with clinical examination (e.g., tapping or balloting a site of suspected injury, then comparing HRV fluctuation to this same function performed on a clinically normal limb).

Given the teachings set forth herein, HRV can also be used as an adjunct in the localization of other pathologic lesions. Pain and/or stress response monitored via HRV during clinical examination, palpation and movement could assist in localization of pathologic lesions. For example, 24 hour readings or another selected time interval can be used to correlate pain and stress associated with specific events (e.g., swallowing, gastric filling, urination, specific movements and the like).

The present invention also provides a method for collection and assessment of HRV data in animals for management of stress levels in animals, especially animals reared in confinement housing, e.g., as a means for enclosure evaluation and environmental management of a preselected confined animal or group of animals, e.g., to increase production. The devices and methods set forth and provided herein are meant to include any animal that can be housed in a confinement situation and can include, e.g., enclosure of animals used in food production, breeding operations, quarantine and/or zoo-like settings, habitats &c.

As used herein, the term "stress" is meant to include, but not be limited to the effect seen from the exertion or application of any external and/or internal stimuli which exerts a negative effect or other wise negatively influences the health status of the subject animal. Specific examples of such stress factors include, e.g., prolonged exposure to unfavorable environmental conditions such as extreme temperatures, over crowding, loud noise, electrical or electromagnetic fields, separation from a companion animal or from an owner, removal from a familiar environment, shipping transport, athletic competition and the like. Other examples of stress related monitoring embodied by the invention include enclosure evaluation and determination of optimal breeding conditions for animals, especially exotics and endangered species as well as determination of well-being of performance and exhibit animals (e.g., circus animals and animal exhibits at zoological parks).

One embodiment of the method for management of stress in a selected group of animals, e.g., a herd or flock, comprises identification of at least one or more sentinel animals from within the herd, establishing a normal R-R interval, LF/HF ratio to show balance between both branches of the autonomic nervous system, or other HRV, data for the sentinel animals and monitoring the sentinel animals for changes in HRV which are indicative of stress. The method can further comprise identification of the etiologic agent which is causing stress in the sentinel animal and attenuation of the etiologic agent to reduce the level of stress seen in the sentinel animal.

For example, in domestic, exotic, marine, and food animals HRV measurements can be used to evaluate stress levels. Optimal HRV values for the selected animal species can initially be determined, e.g., via parallel cortisol studies. Given the teachings set forth herein, HRV can be used as an informative method for evaluation of mental stress and fatigue. In production animals, optimal HRV values can be used to correlate with optimal weight gain and/or rate of production and appropriate measures taken to maintain a selected optimum HRV level in sentinel animals Real time HRV measurements can then be used to identify and evaluate the etiologic factors that cause or produce stress in the selected animal species and also to identify factors which relieve or reduce the stress. Given the teachings and methods set forth herein, HRV monitoring has the capability to give animals a "voice" with respect to their pain and stress status (i.e., as an advocate and conduit for animals to communicate their pain and stress).

In one embodiment of the invention, a method for monitoring stress associated with separation anxiety is provided. A home HRV monitoring unit can be provided, e.g., for household pets, whereby HRV fluctuations would indicate stress levels (e.g., separation anxiety) and then the unit can be used to trigger changes in the environment to reduce stress (e.g., turning on music, activating a sound or other vibration, activating a recording of the animal owner's voice, notification of the veterinarian or other caretaker as to an outpatient's status, or a call to the animal owner's cell phone and the like).

Another embodiment of the invention provides a method for enabling biofeedback of HRV as a tool to train animals through Pavlovian conditioning to positively influence the autonomic nervous system, e.g., to train an animal to calm itself thereby reducing stress, and/or to manage unacceptable behavioral vices such as cribbing, weaving, barking and the like. Animals could be trained to calm themselves or reach a desirable HRV value by rewarding the animal with a stimulus (e.g., click) and a treat when desirable HRV values are approached or reached. Eventually, the animal would only need the stimulus to achieve the desired result (e.g., calming or sedation). This would have many applications in performance animals. This technique could also be used to manage stable vices (e.g., cribbing and weaving). Stalls could be fitted with automatic devices that reward the animal when desirable HRV values are achieved.

Figure 2:
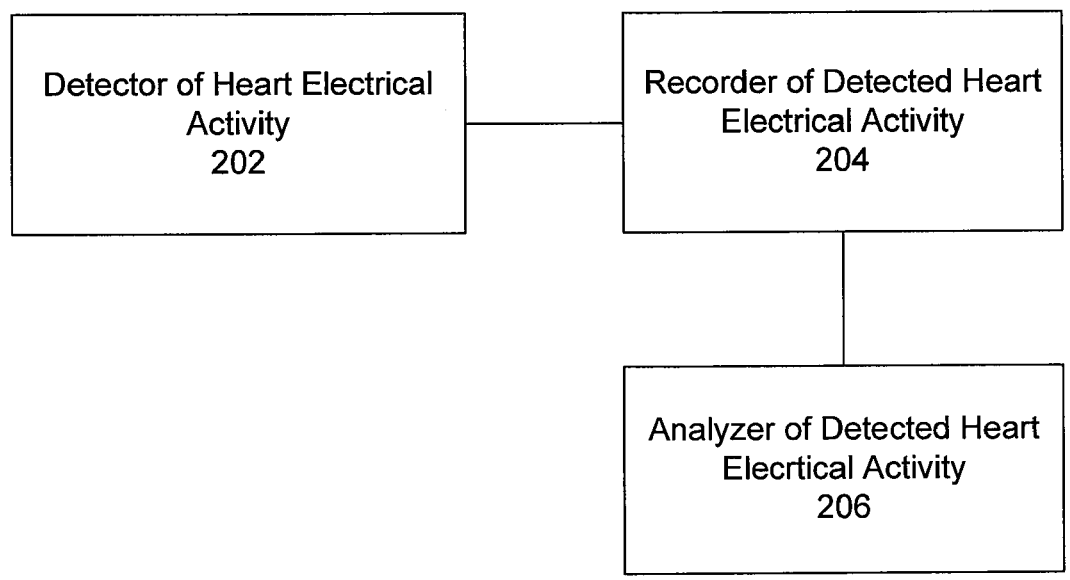
FIG. 2 is a block diagram depiction of an apparatus constructed in accordance with the present invention.

FIG. 1 is a flow diagram of operations performed in accordance with the present invention. In the first operation, illustrated by box 102 in FIG. 1, heart rate for a subject animal over a preselected period of time is determined. In the next operation, illustrated by box 104, the determined heart rate data is analyzed to determine heart rate variability data for a selected heart rate variability parameter and determine whether the preselected condition exists. FIG. 2 is a block diagram depiction of a system 200 constructed in accordance with the present invention. The system includes a detector 202 that detects heart electrical activity in the subject animal. As described above, the detected activity is recorded at a recorder 204 of detected heart electrical activity and an analyzer 206 performs analysis of the detected heart electrical activity. The recorder and analyzer can be separate or integrated into a single apparatus, as noted above.

The foregoing description of a preferred embodiments of the invention has been presented for purposes of illustration and description. It is not intended to be exhaustive or to limit the invention to the precise form disclosed. Obvious modifications or variations are possible in light of the above teachings. The embodiments set forth herein were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A method for detection of a preselected condition unrelated to cardiac arrhythmia in a subject non-human animal from a preselected animal species using heart rate variability analysis comprising the steps of:
   a. determining interbeat interval data for the subject non-human animal over a preselected period of time; and
   b. analyzing the determined interbeat interval data from the subject non-human animal to identify the subject animal's interbeat interval data for a selected heart rate variability (HRV) parameter and thereby determine whether the preselected condition unrelated to cardiac arrhythmia exists, wherein the analyzing step further comprises utilizing an established substantially normal range of values based on at least one of frequency response or time domain response, and an optimal balance profile for the selected heart rate variability parameter of the preselected animal species for clinical evaluation of the preselected animal species, and wherein the determined interbeat interval data is analyzed to determine heart rate variability data for at least one selected heart rate variability parameter to detect the preselected condition unrelated to cardiac arrhythmia.

2. The method of claim 1, wherein the selected heart rate variability parameter is selected from the group consisting of a frequency domain parameter and a time domain parameter.

3. The method of claim 2, wherein the selected heart rate variability parameter is a time domain parameter selected from the group consisting of: heart rate (HR); mean interbeat interval (NN); standard deviation of the inter-beat interval (SDNN); and the square root of the mean squared differences of successive inter-beat intervals (RMS-SD).

4. The method of claim 2, wherein the selected heart rate variability parameter is a frequency domain parameter selected from the group consisting of: total power (TP); very low frequency (VLF); low frequency (LF); high frequency (HF); low frequency to high frequency ratio (LF/HF ratio); normalized low frequency (LF norm); and normalized high frequency (HF norm).

5. The method of claim 1, further comprising the step of comparing the substantially normal range of values for the selected heart rate variability parameter for the preselected animal species to the analyzed heart rate variability data for the selected heart rate variability parameter of the subject animal.

6. The method of claim 1, wherein prior to the analyzing step the method further comprises the step of establishing a substantially normal range of values for the selected heart rate variability parameter for the subject animal.

7. The method of claim 6, further comprising the step of comparing the substantially normal range of values for the selected heart rate variability parameter for the subject animal to the analyzed heart rate variability data for the selected heart rate variability parameter from the selected animal.

8. The method of claim 1, wherein the preselected animal species is selected from the group consisting of: canine, feline, ovine, equine, bovine, caprine, and avian.

9. The method of claim 1, wherein the preselected animal is an exotic animal species.

10. The method of claim 1, wherein the preselected animal species is a fish.

11. The method of claim 1, wherein the preselected animal is an animal in captivity or confinement.

12. The method of claim 1, wherein the preselected condition is stress.

13. The method of claim 12, wherein an etiologic agent producing stress is identified and substantially attenuated or removed from the subject animal to thereby: substantially eliminate stress in the subject animal.

14. The method of claim 12, wherein an etiologic agent producing pain is identified and substantially attenuated, removed or a therapeutic administered to the subject animal to thereby substantially eliminate pain in the subject animal.

15. The method of claim 1, wherein the preselected condition is pain.

16. The method of claim 1, wherein prior to the analyzing step the method further comprises recording the determined interbeat interval data of the subject animal for the preselected period of time.

17. The method of claim 1, wherein prior to the analyzing step the method further comprises the step of establishing an expected range of values for the selected heart rate variability parameter for preselected condition when present in the preselected animal species.

18. The method of claim 1 wherein the animal is a preselected sentinel animal in a group of animals.

19. The method of claim 1, wherein the preselected condition is a subclinical condition.

20. The method of claim 1, wherein the preselected period of time is from, between about 15 seconds to about 20 minutes, but is especially about 10 minutes.

21. The method of claim 1, wherein the preselected period of time is from between about 6 hours and about 36 hours, but is especially about 24 hours.

22. The method of claim 1, further including:
monitoring the selected HRV parameter for an indication of stress levels of the subject non-human animal;
providing a notification of the indicated stress level of the subject non-human animal for initiating a change in environment to reduce the stress levels of the subject non-human animal.

23. The method of claim 22, wherein providing a notification comprises calling a cell phone and providing an indication of the stress level of the subject non-human animal.

24. The method of claim 1, further including:
providing biofeedback training to the subject non-human animal for positively influencing the autonomic nervous system of the subject non-human animal.

25. The method of claim 1, wherein determining interbeat interval data comprises determining R-R interval of the HRV data from the subject animal.

26. The method of claim 1, further including collecting the interbeat interval data from the subject non-human animal using means for detection of electrical activity of the heart.

27. The method of claim 1, further including collecting the interbeat interval data from the subject non-human animal using means for measuring peripheral blood flow to the extremities.

28. A method of detecting a health condition unrelated to cardiac arrhythmia in a selected non-human species, the method comprising:
determining interbeat interval data from a subject non-human animal over a preselected period of time, the interbeat interval data comprising heart rate variability (HRV) data from the subject animal of the selected non-human species;
performing analysis of the collected HRV data to identify time domain and frequency domain signal component parameters of the collected HRV data;
comparing the analysis of the collected HRV data against corresponding analysis of collected HRV data based on at least one of frequency response or time domain response, and an optimal balance profile from at least one substantially normal condition animal of the selected non-human species for clinical evaluation; and
detecting an abnormal health condition unrelated to cardiac arrhythmia in the subject non-human animal based on the comparison.

29. The method of claim 28, wherein performing analysis includes analysis of the interbeat interval data.

30. A method as defined in claim 28, wherein performing analysis includes determining LF/HF ratio of power output components of the collected HRV data.

31. The method of claim 28, further including:
monitoring the HRV data for an indication of stress levels of the subject non-human animal;
providing a notification of the indicated stress level of the subject non-human animal for initiating a change in environment to reduce the stress levels of the subject non-human animal.

32. The method of claim 31, wherein providing a notification comprises calling a cell phone and providing an indication of the stress level of the subject non-human animal.

33. The method of claim 28, further including:
providing biofeedback training to the subject non-human animal for positively influencing the autonomic nervous system of the subject non-human animal.

34. The method of claim 28, wherein determining interbeat interval data comprises determining R-R interval of the HRV data from the subject animal.

* * * * *